United States Patent
Ardaud et al.

(10) Patent No.: US 9,266,811 B2
(45) Date of Patent: Feb. 23, 2016

(54) SYNTHESIS OF (METH)ACRYLIC ANHYDRIDE BY TRANSANHYDRIZATION

(71) Applicant: RHODIA OPERATIONS, Paris (FR)

(72) Inventors: Pierre Marcel Ardaud, Ste Foy les Lyon (FR); Rabih Julien Rached, Millery (FR); Thierry Alban Marcel Vidal, Lyons (FR)

(73) Assignee: Rhodia Operations, Paris (FR)

( * ) Notice: Subject to any disclaimer, the term of this patent is extended or adjusted under 35 U.S.C. 154(b) by 0 days.

(21) Appl. No.: 14/414,899

(22) PCT Filed: Jul. 11, 2013

(86) PCT No.: PCT/EP2013/064698
§ 371 (c)(1),
(2) Date: Mar. 26, 2015

(87) PCT Pub. No.: WO2014/012843
PCT Pub. Date: Jan. 23, 2014

(65) Prior Publication Data
US 2015/0203433 A1    Jul. 23, 2015

(30) Foreign Application Priority Data
Jul. 18, 2012  (FR) ..................... 12 56940

(51) Int. Cl.
*C07C 51/56* (2006.01)
*C07C 51/573* (2006.01)

(52) U.S. Cl.
CPC ............. *C07C 51/56* (2013.01); *C07C 51/573* (2013.01)

(58) Field of Classification Search
None
See application file for complete search history.

(56) References Cited

U.S. PATENT DOCUMENTS

| 4,857,239 | A | 8/1989 | Hurtel et al. | |
|---|---|---|---|---|
| 2002/0161260 | A1 | 10/2002 | Schmitt et al. | |
| 2003/0018217 | A1* | 1/2003 | Dupont et al. | 562/888 |
| 2009/0264673 | A1* | 10/2009 | Broell et al. | 560/204 |
| 2010/0069666 | A1* | 3/2010 | Broell | 562/888 |
| 2010/0317892 | A1* | 12/2010 | Paul et al. | 562/893 |

FOREIGN PATENT DOCUMENTS

| DE | 3510035 A1 | 9/1986 |
|---|---|---|
| EP | 0196520 A1 | 10/1986 |
| EP | 0231689 A1 | 8/1987 |
| EP | 1273565 A1 | 1/2003 |
| GB | 538310 A | 7/1941 |
| WO | WO 2009098422 A1 | 8/2009 |

OTHER PUBLICATIONS

Database Caplus Chemical Abstracts Service, Columbus, Ohio, US; Database Accession No. 1986:610785, Abstract of DE 3510035, Bott et al., BASF A.G., Fed. Rep. Ger. Sep. 25, 1986.*

* cited by examiner

*Primary Examiner* — Karl J Puttlitz
(74) *Attorney, Agent, or Firm* — Osha Liang LLP

(57) ABSTRACT

The present invention relates to a process for preparing an anhydride of formula A-C(=O)—O—(O=)C-A, where A is —CR=CH2 and R is —H or —CH3, comprising: a) a step of reacting an anhydride B—C(=O)—O—(O=)C—B with an acid A-COOH, A being as defined above, wherein the step results in the formation of an anhydride A-C(=O)—O—(O=)C—B and of an acid B—COOH, A and B being such that said acid B—COOH is more volatile than said acid A-COOH, and b) a step of reacting said anhydride A-C(=O)—O—(O=)C—B with the acid A-COOH under conditions such that the amount of acid B—COOH is less than the amount of acid A-COOH, resulting in the formation of the anhydride A-C(=O)—O—(O=)C-A, in which said reaction steps are carried out in the presence of an acid catalyst which is more volatile than said anhydride A-C(=O)—O—(O=)C-A.

11 Claims, 2 Drawing Sheets

SYNTHESIS OF (METH)ACRYLIC ANHYDRIDE BY TRANSANHYDRIZATION

CROSS-REFERENCE TO RELATED APPLICATIONS

This application is a U.S. national stage entry under 35 U.S.C. §371 of International Application No. PCT/EP2013/064698 filed Jul. 11, 2013, which claims priority to French Application No. 1256940 filed on Jul. 18, 2012, the whole content of this application being herein incorporated by reference for all purposes.

TECHNICAL FIELD OF THE INVENTION

The present invention relates to a process for the preparation of a (meth)acrylic anhydride by reaction of a (meth)acrylic acid with an anhydride other than a (meth)acrylic anhydride, according to a "transanhydrization" reaction.

(Meth)acrylic anhydrides are conventionally prepared by a transanhydrization reaction, typically by reaction of (meth)acrylic acid with acetic anhydride, whereby acetic acid and the desired anhydride are formed. The acetic acid formed is generally removed by distillation as it is formed. This type of reaction, which is well known, is described, for example, in Application EP 1 273 565.

In addition to the preparation of the desired (meth)acrylic anhydride, by-products are formed, in particular polymerization products and addition products, which require a purification of the (meth)acrylic anhydride formed. The content of these by-products can be reduced in a way known per se by the addition of polymerization inhibitors. Nevertheless, even on employing such inhibitors, by-products continue to be formed. Typically, these by-products are removed by distillation, which is a problematic operation, in particular in view of the lachrymatory nature of the (meth)acrylic anhydride.

Processes for the synthesis of (meth)acrylic anhydride of batch type (noncontinuous batchwise processes) have in particular been described, for example in Application EP 0 231 689.

Alternatively, more advantageous continuous and semi-continuous processes have also been provided, in particular in EP 1 237 565 or US 2009/0264673, and make it possible to reduce the presence of by-products.

Furthermore, the use of catalysts has been envisaged for improving the reaction. In this context, essentially, it is heterogeneous catalysts which have been envisaged, in particular in US 2002/0161260, and which can present difficulties in terms of extrapolation or of material transfer. More occasionally, homogeneous catalysts have been provided, such as, for example, the sulfuric acid described in DE 3510035, which do not present this type of difficulty but which, in return, generally exhibit a major disadvantage, namely that they generally involve awkward post-treatment stages in order to be separated from the anhydride. Thus, these catalysts do not result systematically in an improvement in the yield and in addition often exhibit the disadvantage of having to be removed on conclusion of the reaction. One aim of the present invention is to provide a process for the preparation of (meth)acrylic anhydride which avoids awkward stages of post-treatment of the anhydride, in particular awkward stages of removal of the catalyst used.

The present invention is also targeted at providing an effective process for the preparation of (meth)acrylic anhydride which can, if need be, be carried out according to a continuous mode, avoiding the awkwardnesses and disadvantages of the processes of batch type.

SUMMARY OF THE INVENTION

To this end, the present invention provides for the use of a specific catalyst, namely an acid catalyst which is more volatile than the (meth)acrylic anhydride synthesized.

More specifically, a subject-matter of the present invention is a process for the preparation of an anhydride of formula A-C(=O)—O—(O=)C-A, where A is —CR=$CH_2$ and R is —H or —$CH_3$, comprising:

a) a stage of reaction of an anhydride B—C(=O)—O—(O=)C—B with an acid A-COOH, A being as defined above, this stage resulting in the formation of an anhydride A-C(=O)—O—(O=)C—B and of an acid B—COOH, A and B being such that said acid B—COOH is more volatile than said acid A-COOH, and b) a stage of reaction of said anhydride A-C(=O)—O—(O=)C—B with the acid A-COOH under conditions such that the amount of acid B—COOH is less than the amount of acid A-COOH, resulting in the formation of the anhydride A-C(=O)—O—(O=)C-A, in which said reaction stages are carried out in the presence of an acid catalyst which is more volatile than said anhydride A-C(=O)—O—(O=)C-A.

DETAILED DESCRIPTION OF THE INVENTION

In the context of the present description, the anhydrides corresponding to the formula A-C(=O)—O—(O=)C-A, where A is —CR=$CH_2$ and R is —H or —$CH_3$, are denoted by the generic term of "(meth)acrylic" anhydrides. A (meth)acrylic anhydride within the meaning of the invention also denotes a mixture of such anhydrides.

More generally, the term "(meth)acrylic" is employed in the present description as synonym for the expression "acrylic and/or methacrylic". Thus, when reference is made to a (meth)acrylic acid, this term denotes acrylic acid $CH_2$=CH—COOH or methacrylic acid $CH_2$=C($CH_3$)—COOH or alternatively a mixture of these two acids. In the same way, if reference is made to a (meth)acrylic anhydride, the intention is to denote an acrylic anhydride $CH_2$=CH—C(=O)—O—(O=)C=CH—$CH_2$, a methacrylic anhydride $CH_2$=C($CH_3$)—C(=O)—O—(O=)C=C($CH_3$)=$CH_2$, a mixed acrylic and methacrylic anhydride $CH_2$=CH—C(=O)—O—(O=)C=C($CH_3$)=$CH_2$ or else a mixture of these anhydrides.

The process of the invention makes it possible to prepare the various entities corresponding to the term "(meth)acrylic anhydride", namely, according to preference, acrylic anhydride, methacrylic anhydride or a mixture of the two, by choice of the acid A-COOH employed in the process.

According to an advantageous embodiment, the (meth)acrylic anhydride prepared according to the invention is either an acrylic anhydride $CH_2$=CH—C(=O)—O—(O=)C=CH=$CH_2$ or a methacrylic anhydride $CH_2$=C($CH_3$)—C(=O)—O—(O=)C=C($CH_3$)=$CH_2$, respectively starting from acrylic acid or methacrylic acid as acid A-COOH. However, it is not ruled out, according to a more specific embodiment, to start from a mixture of acrylic and methacrylic acids.

According to the invention, the process for the preparation of the (meth)acrylic anhydride comprises a stage, denoted a), of reaction of an anhydride B—C(=O)—O—(O=)C—B with an acid A-COOH, where A and B are such that the acid B—COOH is more volatile than the acid A-COOH.

Within the meaning of the present invention, the expression "a first compound is more volatile than a second compound" means that the first compound has a lower boiling point than that of the second compound, under the pressure conditions of the stage under consideration.

The choice of an anhydride B—C(=O)—O—(O=)C—B such that B—COOH is more volatile than A-COOH results in each of the products which can be formed during the reaction stage being more volatile than the (meth)acrylic anhydride A-C(=O)—O—(O=)C-A. The latter, which is less volatile, is then generally easier to isolate from the remainder of the compounds present, during subsequent treatment stages.

This stage a) results in the formation of a compound of mixed anhydride type A-C(=O)—O—(O=)C—B, which is more volatile than the anhydride A-C(=O)—O—(O=)C-A, and of an acid B—COOH.

According to the invention, the process for the preparation of the (meth)acrylic anhydride also comprises a stage, denoted b), of reaction of said anhydride A-C(=O)—O—(O=)C—B with the acid A-COOH under conditions such that the amount of acid B—COOH is less than the amount of acid A-COOH.

Under such conditions, stage b) results in the formation of the anhydride A-C(=O)—O—(O=)C-A.

This is because, when the amount of acid B—COOH is less than the amount of acid A-COOH, the equilibrium of the reaction tends towards the formation of the desired anhydride. Thus, the mixed anhydride A-C(=O)—O—(O=)C—B reacts with the acid A-COOH, resulting in the formation of the anhydride A-C(=O)—O—(O=)C-A and of acid B—COOH.

If such conditions are not adhered to, then the mixed anhydride may not react with the acid A-COOH to form the anhydride A-C(=O)—O—(O=)C-A; it may thus be found among the final products.

Thus, during the process, when the amount of acid B—COOH becomes greater than the amount of acid A-COOH, the second reaction stage can no longer take place. Both anhydride A-C(=O)—O—(O=)C-A and mixed anhydride A-C(=O)—O—(O=)C—B are then obtained among the final products. The fact that the mixed anhydride A-C(=O)—O—(O=)C—B is more volatile than the anhydride A-C(=O)—O—(O=)C-A makes it possible to easily separate it from the latter.

In the context of the invention, the reaction stages a) and b) can take place simultaneously or sequentially.

The two combined reaction stages a) and b) of the process according to the invention can be denoted by "transanhydrization reaction".

Thus, the (meth)acrylic anhydride is formed according to a transanhydrization reaction, that is to say starting from the (meth)acrylic acid and from an anhydride B—C(=O)—O—(O=)C—B different from the desired anhydride and resulting in the desired (meth)acrylic anhydride and a carboxylic acid B—COOH different from the initial acid, with the anhydride A-C(=O)—O—(O=)C—B as intermediate compound between the initial and final anhydrides.

It is possible to associate, with this transanhydrization reaction, a reaction region which delimits the space in which the two stages a) and b) take place.

Thus, different compounds can be present in the reaction region and on exiting this region.

More specifically, at a given instant, the reaction region generally comprises anhydride B—C(=O)—O—(O=)C—B, acid A-COOH, the catalyst, the mixed compound A-C(=O)—O—(O=)C—B, acid B—COOH and anhydride A-C(=O)—O—(O=)C-A. All of these compounds can also be present on exiting the reaction region.

This is because, as indicated above, the reactants B—C(=O)—O—(O=)C—B and A-COOH, and also the catalyst, react in the reaction region to form first the mixed anhydride A-C(=O)—O—(O=)C—B and the acid B—COOH. Then, if the amount of acid B—COOH is less than that of acid A-COOH, the mixed anhydride then reacts with the acid A-COOH and anhydride A-C(=O)—O—(O=)C-A is formed.

According to the invention, stages a) and b) are carried out in the presence of an acid catalyst which is more volatile than the anhydride A-C(=O)—O—(O=)C-A synthesized.

The choice of a more volatile acid catalyst makes possible extremely easy removal of the catalyst, on one hand, and of the anhydride synthesized, on the other hand, by simple evaporation of the catalyst, which is particularly advantageous. The anhydride synthesized is then obtained in a purified form and can optionally be further purified, in the case where a certain amount of catalyst is still present, by an additional treatment, for example with active charcoal.

Mention may in particular be made, as acid catalyst which can be used according to the invention, of trifluoroacetic acid (TFA), of formula $CF_3$—COOH, or trifluoromethanesulfonimide, also known as triflimide, of formula $(CF_3$—$SO_2)_2$—NH, or else trifluoromethanesulfonic acid, also known as triflic acid, of formula $CF_3$—$SO_2$—OH.

Preferably, the acid catalyst used is triflic acid.

Triflic acid has the advantage of being a particularly reactive catalyst, bringing about a low residence time in the reaction region and allowing the process to be implemented continuously, as explained later in the description.

According to the invention, the acid B—COOH formed is more volatile than the anhydride A-C(=O)—O—(O=)C-A formed. The separation of the anhydride on conclusion of the reaction is then very easy, given that both the catalyst and the acid formed are more volatile than the anhydride formed.

According to the invention, the anhydride B—C(=O)—O—(O=)C—B and the acid A-COOH are more volatile than the anhydride prepared. The anhydride formed is thus less volatile than the reactants, which facilitates its isolation, even when a certain amount of reactants have not reacted and are found among the compounds formed during the reaction.

Thus, the anhydride B—C(=O)—O—(O=)C—B, the acid A-COOH and the acid B—COOH are more volatile than the anhydride A-C(=O)—O—(O=)C-A formed. The anhydride formed is thus the least volatile compound among the products and reactants and its isolation is accordingly easier.

According to one embodiment, the acid B—COOH is removed during stages a) and b).

This is because, as mentioned above, during stage b), the mixed anhydride A-C(=O)—O—(O=)C—B can react with the acid A-COOH to give the desired anhydride A-C(=O)—O—(O=)C-A, if the amount of acid B—COOH is less than that of acid A-COOH. Consequently, in order to obtain such conditions and to shift the equilibrium of the reaction towards the formation of the desired anhydride, the acid B—COOH formed can be removed during stages a) and b), that is to say withdrawn from the reaction region.

The gradual removal of the acid B—COOH thus makes it possible to obtain conditions which make possible the formation of the desired anhydride A—(C=O)—O—(C=O)-A.

The removal of the acid B—COOH is, for example, carried out by distillation.

According to one embodiment, the acid catalyst is less volatile than the acid B—COOH.

This embodiment is advantageous as the acid catalyst is then not only separable from the anhydride A-C(=O)—O—(O=)C-A synthesized but also from the acid B—COOH formed. The catalyst can thus be directly recyclable and reusable in the reaction stages, as described later.

When the acid catalyst used is more volatile than the acid B—COOH, the catalyst can also be recycled by a stage of subsequent treatment of the effluents comprising the acid B—COOH.

The catalyst can thus be recovered, recycled and reused in the process according to the invention.

According to one embodiment, stages a) and b) of the process are carried out continuously.

In the context of the present description, the term "process carried out continuously" or more simply "continuous process" is understood to mean a process for which the different successive operations follow on from each other without interruption and consequently in which the product, in this instance (meth)acrylic anhydride, is prepared uninterruptedly.

Thus, according to this embodiment, the reactants are introduced continuously and the compounds liable to be obtained are recovered also continuously. The process of the invention can thus either be carried out noncontinuously and is then denoted by "batch process" or "batchwise process" or can be carried out continuously and is then denoted by "continuous process".

According to one embodiment, the molar mass of B is less than the molar mass of A.

Advantageously, B is a methyl or ethyl group.

Preferably, B is a methyl group.

The preparation of the (meth)acrylic acid is thus typically carried out by reaction of a (meth)acrylic acid with acetic anhydride.

For example, methacrylic acid is prepared by reaction of methacrylic acid with acetic anhydride According to one embodiment, the reaction stages a) and b) are carried out at a temperature of 60° C. to 120° C., advantageously of 70° C. to 110° C. and preferably of 90° C. to 100° C.

This is because, the more the temperature increases, the faster the reaction kinetics. On the other hand, the more the temperature increases, the more the compounds present decompose.

Thus, the temperature of the reaction stages is chosen in order to have sufficiently fast kinetics, while avoiding excessively great decomposition of the compounds.

According to one embodiment, the reaction stages a) and b) are carried out at a pressure of 0.01 bar to 3 bar, advantageously of 0.5 bar to 1.5 bar and preferably at atmospheric pressure.

Within the meaning of the present invention, the term "atmospheric pressure" is understood to mean the ambient pressure which prevails under the conditions of the process, equal to 1 bar or close to 1 bar.

The process can be carried out whatever the pressure but it is particularly advantageous to operate at atmospheric pressure, given that this makes it possible to dispense with any control of the pressure.

Advantageously, the molar ratio of the acid A-COOH to the anhydride B—C(=O)—O—(O=)C—B is from 0.5 to 5, advantageously from 1.5 to 3, preferably less than 2.5 and more preferably still less than 2.

Advantageously, the ratio of the weight of acid catalyst to the total weight of the reactants B—C(=O)—O—(O=)C—B and A-COOH is from 5 ppm to 1%, advantageously from 20 ppm to 100 ppm.

According to one embodiment, the process comprises a stage of extraction of the acid catalyst and of the acid B—COOH formed, in order to separate the acid catalyst and the acid B—COOH, in particular by distillation.

This extraction stage takes place after stages a) and b).

On conclusion of the transanhydrization reaction, the main compounds present are the acid catalyst, the acid B—COOH and the anhydride A-C(=O)—O—(O=)C-A. Thus, the acid catalyst and the acid B—COOH formed are extracted, in particular by distillation, in order to isolate the anhydride A-C(=O)—O—(O=)C-A and to recycle, if appropriate, the catalyst in order for it to be reusable. In this case, the catalyst can be reused in the abovementioned reaction stage.

It is thus possible to define an extraction region delimiting the space in which the extraction stage takes place. The reaction and extraction regions can be separate, be coincident or overlap, as described later.

Advantageously, after the extraction stage, the acid catalyst is recovered and recycled in order to be used in the stage of reaction of the acid A-COOH with the anhydride B—C(=O)—O—(O=)C—B.

Various treatments which make it possible to recover the catalyst in the catalyst/acid B—COOH mixture extracted after the reaction stage can be envisaged. Preferably, the recovery of the catalyst is carried out by distillation.

As indicated above, when the acid catalyst is less volatile than the acid B—COOH, the separation between the catalyst and the acid B—COOH is easier. This separation is typically carried out by distillation.

The reaction stages are generally carried out in a reactor.

This reactor then defines the reaction region. It is generally a plug-flow reactor or a stirred continuous reactor, or also a cascade of stirred continuous reactors.

Advantageously, the extraction stage is carried out in a distillation column.

This column then defines the extraction region.

The column has, for example, from 10 to 30 theoretical plates and more specifically, for example, 20 theoretical plates.

As a result of the differences in volatility between the various compounds obtained, the (meth)acrylic anhydride, the least volatile compound of all, is recovered at the column bottom, whereas the acid catalyst and the acid B—COOH are recovered at the column top. If, in addition, the catalyst is less volatile than the acid B—COOH, it is recovered before the acid B—COOH, which is itself recovered at the column top.

The extraction stage can also be carried out in several successive columns connected to one another.

According to one embodiment, the reaction stages a) and b) are carried out in a reactor and the extraction stage is carried out in one or more successive distillation columns separate from the reactor.

Thus, the various reactants, namely B—C(=O)—O—(O=)C—B, A-COOH and the catalyst, react within the reactor, in the reaction region, to form the anhydride A-C(=O)—O—(O=)C—B, the acid B—COOH and the desired (meth)acrylic anhydride quantitatively, if the required conditions are adhered to. Since the reactor is connected to the distillation column, as stages a) and b) take place in the reactor, the various products (A-C(=O)—O—(O=)C-A, B—COOH and possibly A-C(=O)—O—(O=)C—B) and/or the reactants migrate towards the distillation column, defining the extraction region, which makes it possible to separate the anhydride formed from the other compounds present.

The reactor and the column are then separate entities.

Thus, even if the reactor is separate from the column, when the two entities are connected, the transanhydrization reaction can also take place in the column. The reaction and extraction regions are thus then initially separate but can overlap.

The advantage of this embodiment lies in the possibility of choosing the reaction parameters within the reactor (such as the temperature, the pressure or the amounts of reactants) independently of the separation conditions in the column.

According to another embodiment, the reaction stages a) and b) and the extraction stage are carried out in one or more successive distillation columns. According to this embodiment, the three stages are carried out within one and the same chamber. The reaction and extraction regions are thus then coincident.

Thus, the various reactants are directly introduced within the column, for example at the middle of the column, and react in order to form the (meth)acrylic anhydride, and also the other products (B—COOH, A-C(=O)—O—(O=)C—B). As these compounds are formed, they are subjected to the extraction stage which makes it possible to separate them. This is then referred to as reactive distillation.

According to this embodiment, even if the catalyst is more volatile than the anhydride A-C(=O)—O—(O=)C-A, it is generally entrained towards the column bottom, mixed with the anhydride A-C(=O)—O—(O=)C-A. The separation of these two compounds can then be carried out in various ways, in particular easily by distillation, given that the catalyst is more volatile than the (meth)acrylic anhydride.

As indicated above, according to one embodiment, the catalyst is triflic acid. In point of fact, triflic acid is particularly suitable for the process according to the invention, whether the latter is batchwise or continuous.

This is because triflic acid is particularly reactive and results in rapid formation of (meth)acrylic anhydride. Thus, at the outlet of the reactor or directly within the distillation column, a significant amount of mixed anhydride A-C(=O)—O—(O=)C—B is rapidly obtained. This thus makes it possible, after extraction of the catalyst and of the acid B—COOH, to obtain a significant yield of (meth)acrylic anhydride, typically of greater than 50%, advantageously of greater than 75% and preferably from 80% to 95%, with respect to the amount of anhydride B—C(=O)—O—(O=)C—B initially introduced.

As indicated above, triflic acid, by virtue of its high reactivity, brings about a shorter residence time in the reaction region. Thus, when the process is carried out batchwise, the amount of by-products is reduced and the yield of the process improved. The implementation of the process of the invention batchwise and using triflic acid is thus particularly advantageous.

Furthermore, when the process is carried out continuously, triflic acid, due to its low residence time in the reaction region, brings about a smaller scale, which is advantageous in terms of equipment.

The use of triflic acid thus makes it possible to carry out the process batchwise or continuously, in separate reactors (transanhydrization reaction, followed by extraction) or in a single distillation column with intersected streams of reactants and effluents.

According to one embodiment, one or more polymerization inhibitors can be introduced during the process in order to limit the formation of by-products, such as polymers based on (meth)acrylic acid and/or on (meth)acrylic anhydride.

They can then be introduced with the acid A-COOH into the reaction region and/or into the extraction region.

Advantageously, these inhibitors are introduced into the extraction region. This is because they are particularly effective in the extraction region and make it possible in particular to prevent the condensation reactions liable to take place therein.

Preferably, when the extraction region consists of a distillation column, the inhibitors are introduced at the column top.

The inhibitors have to be active with regard to the polymerization while being inert with regard to the (meth)acrylic anhydrides and acid.

They can in particular be chosen from hydroquinone, hydroquinone monomethyl ether, topanol A, phenothiazine and hydroxytetramethylpiperidinoxyl (hydroxy-TEMPO).

Brief Description Of The Drawings

A better understanding of the invention will be obtained on reading the description which will follow, given solely by way of example and made with reference to the appended drawings, in which.

The anhydride B—C(=O)—O—(O=)C—B, denoted (I), the acid A-COOH, denoted (II), and a catalyst C more volatile than the anhydride A-C(=O)—O—(O=)C-A, denoted (I'), are injected into the reactor 1. Stage a) takes place in the reaction region R and results in the formation of the mixed anhydride A-C(=O)—O—(O=)C—B, denoted (III), and the acid B—COOH, denoted (II'). In order for stage b) to be able to take place, the acid (II') is removed as it is formed in order for its amount in the region R to be less than that of the acid (II). Stage b) then takes place in the region R and results in the formation of the anhydride (I').

At the outlet of the reactor 1, the reactants (I), (II) and C, the intermediate compound (III) and the products (1') and (II') are conveyed to the distillation column 2. As the anhydride (I') is less volatile than all the other compounds, the acid (II'), the mixed anhydride (III) and also the catalyst C are easily extracted from the mixture. The acid (II') is recovered at the column top, and the anhydride (III) and the majority of the catalyst C are recovered and reinjected via the loop 3 into the reactor 1. The reactants (I) and (II) are also recovered and reinjected via the loop 3 into the reactor 1. The anhydride (1') is recovered at the column bottom with a very small amount of catalyst C ($\epsilon$C), typically of less than 10 ppm, indeed even 5 ppm, and thus non-reactive.

Figure 1:
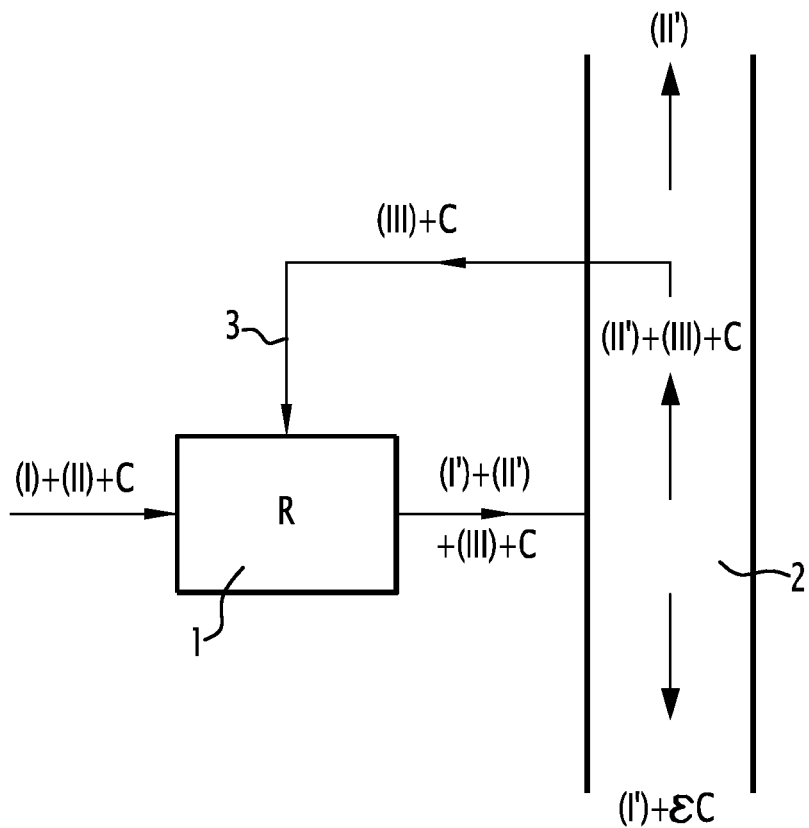
FIG. 1 is a view in cross-section along a median vertical plane of a device in which the process according to the invention is carried out, composed of a reactor 1 connected to a distillation column 2, again connected to the reactor 1 via a reinjection loop 3. The reactor 1 comprises a reaction region R.
Figure 2:
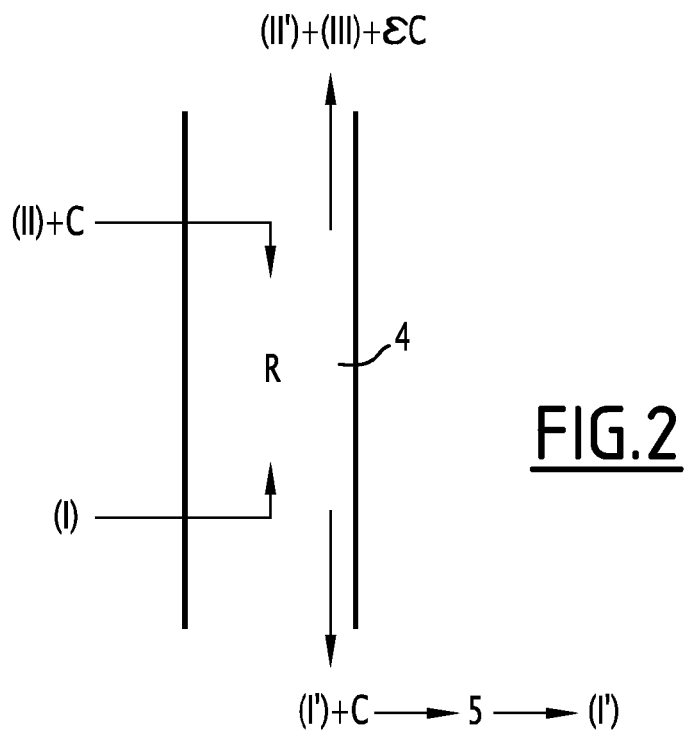

FIG. 2 is a view in cross-section along a median vertical plane of a device composed of a single distillation column 4 in which the process according to the invention is carried out in the form of a reactive distillation.

The acid A-COOH, denoted (II), and the catalyst C are injected at the top of the column 4, and the anhydride B—C(=O)—O—(O=)C—B, denoted (I), is injected at the bottom of the column 4. The various reactants meet in the reaction region R.

Stage a) takes place and results in the formation of the mixed anhydride A-C(=O)—O—(O=)C—B, denoted (III), and the acid B—COOH, denoted (II'). As a result of the differences in volatility which exist, the acid (II') is systematically removed as it is formed and its amount in the region R is thus less than that of the acid (II). Stage b) can then take place and results in the formation of the anhydride A-C(=O)—O—(O=)C-A, denoted (I').

The acid (II') and the mixed anhydride (III), which are more volatile than the anhydride (I'), are extracted and recovered at the column top as stages a) and b) take place. The majority of the catalyst C, although it is more volatile than the anhydride (I'), is entrained towards the column bottom, mixed with the anhydride (I'). Thus, only a small amount of catalyst C is recovered at the column top (εC). After having been recovered at the column bottom, the anhydride (I') and the catalyst C can be separated in a device 5, for example a second distillation column, in order to isolate the anhydride (I').

Figure 3:
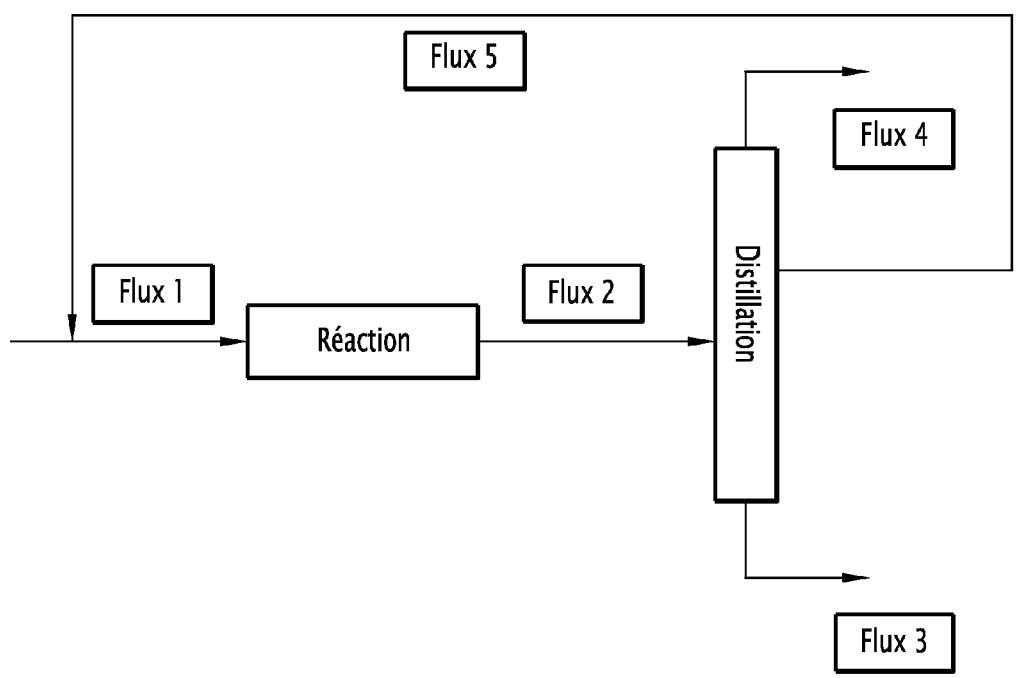

FIG. 3 is a scheme of the device used in example 3.

EXAMPLES

Example 1

200 g of acetic anhydride, 337 g of methacrylic acid, 2.68 g of phenothiazine and a known amount of triflic acid, shown in table 1, were introduced into a mechanically stirred 1-liter jacketed glass reactor. The temperature was maintained between 85° C. and 95° C. according to the tests, at atmospheric pressure.

Samples were subsequently taken over time in order to compare the tests with one another as regards the time for achieving equilibrium.

| No. of the test | Amount of triflic acid | MA/Ac$_2$O molar ratio | Temperature (° C.) | Time for achieving equilibrium (min) |
|---|---|---|---|---|
| 1 | 0 | 2 | 85 | 105 |
| 2 | 25 ppm | 2 | 85 | 17 |
| 3 | 50 ppm | 2 | 85 | 12 |
| 4 | 50 ppm | 2 | 95 | 7 |

Example 2

The feeding of the reactants and the operating conditions are those described in test 4 of example 1. Phenothiazine was also added as polymerization inhibitor. On the other hand, the reaction was carried out continuously in a tubular reactor with a diameter of ⅛ and a length sufficient to achieve equilibrium at the outlet. This stream was used to feed a column of 10 to 15 plates. The column had a diameter of 3 cm and the vacuum of 20 mbar was provided by a vane pump.

The 537 g/h of crude product which were obtained are divided as follows: 116 g/h at the column bottom and 421 g/h in the remainder of the column. The product recovered at the bottom comprised 96% methacrylic anhydride, 1.5% mixed anhydride (A-C(=O)—O—(O=)C—B), 1% inhibitor and 1.5% unknown compounds.

A continuous feed of phenothiazine was employed at the column top in order to prevent polymerization in the column. The operating pressure was 20 mbar at the top and the temperature of the bottom was 93° C.

Example 3

Acrylic anhydride CH$_2$=CH—C(=O)—O—(O=)C=CH=CH was prepared according to the process of the invention by reaction between acrylic acid and acetic anhydride. The sequence of appliances is represented in FIG. 3.

In the reaction region, the reaction temperature was set at 100° C. and the pressure was set at atmospheric pressure.

In the distillation (extraction) region, the pressure was set at 20 mbar absolute and a temperature gradient (between 90° C. at the column bottom and 25° C. at the column top) was observed.

As indicated in FIG. 3, the reaction region was fed with the stream 1, with an overall flow rate of 2 kg/h and composed of the recycling stream 5 and of a continuous feed of a fresh mixture of acetic anhydride, acrylic acid and triflic acid.

The adjustments of the stream 1, composed of the stream of fresh mixture and of the stream 5, were such that, in the reaction region, there was continuously:

acetic anhydride: incoming flow rate of 795 g/h (7.794 mol/h), acrylic acid: incoming flow rate of 1004 g/h (13.95 mol/h), and triflic acid at 50 ppm by weight, with respect to the combination {acetic anhydride+acrylic acid}.

At the outlet of this reaction region, the stream 2 essentially conveyed acrylic anhydride, acetic acid, triflic acid and mixed acrylic/acetic anhydride towards the distillation column.

Under the conditions described above, the acrylic anhydride, with a purity of greater than 95%, was recovered in the stream 3 with a flow rate of approximately 840 g/h (6.66 mol/h). At the column top, the stream 4 (950 g/h, 14.8 mol/h) was very predominantly (>95% by weight) composed of acetic acid. The recycling stream 5 essentially transported triflic acid and mixed acrylic/acetic anhydride in order to reinject them into the reaction region.

The invention claimed is:

1. A process for the preparation of an anhydride of formula A-C(=O)—O—(O=)C-A, where A is —CR=CH$_2$ and R is —H or —CH$_3$, comprising:
   a) a stage of reaction of an anhydride B—C(=O)—O—(O=)C—B with an acid A-COOH, A being as defined above, this stage resulting in the formation of an anhydride A-C(=O)—O—(O=)C—B and of an acid B—COOH, A and B being such that said acid B—COOH is more volatile than said acid A-COOH, and
   b) a stage of reaction of said anhydride A-C(=O)—O—(O=)C—B with the acid A-COOH, under conditions such that the amount of acid B—COOH is less than the amount of acid A-COOH, resulting in the formation of the anhydride A-C(=O)—O—(O=)C-A,
   in which said reaction stages are carried out in the presence of an acid catalyst which is more volatile than said anhydride A-C(=O)—O—(O=)C-A.

2. The process as claimed in claim 1, in which the acid B—COOH is removed during the reaction stages a) and b).

3. The process as claimed in claim 1, carried out continuously.

4. The process as claimed in claim 1, in which the molar mass of B is less than the molar mass of A.

5. The process as claimed in claim 1, in which B is a methyl or ethyl group and in particular a methyl group.

6. The process as claimed in claim 1, in which the acid catalyst is triflic acid.

7. The process as claimed in claim 1, in which the reaction stages a) and b) are carried out at a temperature of 60° C. to 120° C.

8. The process as claimed in claim 1, in which the reaction stages a) and b) are carried out at a pressure of 0.01 bar to 3 bar.

9. The process as claimed in claim 1, comprising a stage of extraction of the acid catalyst and of the acid B—COOH formed, in order to separate the acid catalyst and the acid B—COOH, in particular by distillation.

10. The process as claimed in claim 9, in which the reaction stages are carried out in a reactor and the extraction stage is carried out in one or more successive distillation columns separate from the reactor.

11. The process as claimed in claim 9, in which the reaction stages and the extraction stage are carried out in one or more successive distillation columns.

* * * * *